(12) United States Patent
Dismukes et al.

(10) Patent No.: US 6,803,474 B1
(45) Date of Patent: Oct. 12, 2004

(54) MN₄O₄-CUBANE TYPE CATALYSTS

(75) Inventors: Gerard C. Dismukes, Princeton, NJ (US); Wolfgang F. Ruettinger, Plainsboro, NJ (US)

(73) Assignee: The Trustees of Princeton University, Princeton, NJ (US)

(*) Notice: Subject to any disclaimer, the term of this patent is extended or adjusted under 35 U.S.C. 154(b) by 286 days.

(21) Appl. No.: 10/008,822

(22) Filed: Nov. 13, 2001

Related U.S. Application Data (62) Division of application No. 09/347,629, filed on Jul. 2, 1999, now Pat. No. 6,316,653.
(60) Provisional application No. 60/131,663, filed on Apr. 29, 1999, and provisional application No. 60/091,819, filed on Jul. 6, 1998.

(51) Int. Cl.⁷ .......................... C07F 13/00; B01J 31/00; C01B 7/00; C01B 15/01
(52) U.S. Cl. ...................... 556/20; 556/45; 556/49; 502/150; 502/162; 423/502; 423/584
(58) Field of Search ................. 556/20, 45, 49; 502/150, 162; 423/502, 584

(56) References Cited

U.S. PATENT DOCUMENTS

| | | | | |
|---|---|---|---|---|
| 4,455,203 A | * | 6/1984 | Stucki | 205/468 |
| 4,711,772 A | * | 12/1987 | Jacobson | 423/584 |
| 5,871,707 A | * | 2/1999 | Hibi et al. | 423/502 |

FOREIGN PATENT DOCUMENTS

EP          0 331 465    *   9/1989

OTHER PUBLICATIONS

Ruettinger, et al., "Synthesis and Characterization of Mn4O4L6 Complexes with Cubane–Like Core Structure: A New Class of Models of the Active Site of the Photosynthesis Water Oxidase," Journal of the American Chemical Society, vol. 119, No. 28, pp. 6670–6671.
Aromi, et al., "Manganese Carboxylate Clusters: From Structural Aesthetics to Single–Molecule Magnets," Polyhedron, vol. 17, No. 17, pp. 3005–3020, 1998.
Aromi, et al., "Modeling the Photosyntehtic Water Oxidation Complex: Activation of Water by Contolled Deprotonation and Incorporation into a Tetranuclear Manganese Complex," Am. Chem. Soc., vol. 120, pp. 5850–5851, 1998.
Libby, et al., "Preparation and Properties of Models for the Photosynthetic Water Oxidation Center: Spin Frustration in the [Mn4O2(O2CR)7(pic)2] Anion,"Inorg. Chem. vol. 30, No. 18, pp. 3486–3495, 1991.
Manchanda, et al., High–Valent Oxomanganese Clusters: Structural and Mechanistic Work Relevant to the Oxygen-Evolving Center in Photosystem II, Coordination Chemistry Reviews 144 (1995), pp. 1–38.

Taft, et al., "Iron and Manganese Alkoxide Cubes," J. Am. Chem. Soc. vol. 115, No. 25, pp. 11753–11766, 1993.
Ruttinger, et al., "Synthetic Water–Oxidation Catalysts for Artificial Photosynthetic Water Oxidation," Chemical Reviews, vol. 97, No. 1, pp. 1–24, 1997.
Dimitrou, et al., "[Co₄O₄]⁴⁺ Cubane Core as a Brønsted Base: Preparation and Properties of [Co₄O₃(OH)(O₂CR)₂(bpy)₂]³⁺ and [Co₄O₂(OH)₂(O₂CR)₂(bpy)₂]⁴⁺ Salts," Inorg. Chem. 1999, 38, pp. 1834–1841.
Dimitrou, et al., ""Dimerization" of the [Co$^{III}_2$(OH)₂] Core to the First Example of a [Co$^{III}_4$O₄] Cubane: Potential Insights into Photsynthetic Water Oxidation," J. Am. Chem. Soc. 1993, 115, pp. 6432–6433.
Dismukes, et al., "Structure of the Mn₄Ca₁ Core of the PSII Water Oxidizing Complex and the Mn₄O₄ –Cubane/Mn₄O₂ –Butterfly Model Complexes," Photosynthesis: Mechanisms and Effects, vol. II, pp. 1259–1266, (1998).
Law, et al., "Manganese Redox Enzymes and Model Systems: Properties, Structures, and Reactivity," Advances in Inorganic Chemistry, vol. 46, pp. 305–440.
Ruettinger, et al., "Oxidation/Dehydrogenation Catalysis With Reactive Manganese–OXO Cubanes," Abstracts of Papers of the American Chemical Society, 216:441–INOR, (1998).
Ruettinger, et al., "Protonation and Dehydration Reactions of the Mn₄O₃L₆ Cubane and Synthesis and Crystal Structure of the Oxidized Cubane [Mn₄O₄L₆]⁺ : A Model for the Phososynthetic Water Oxidizing Complex," Inorg. Chem. 1999, 38, pp. 1036–1037.

* cited by examiner

*Primary Examiner*—Porfirio Nazario-Gonzalez
(74) *Attorney, Agent, or Firm*—Wolff & Samson PC (57) ABSTRACT

Highly reactive, stable tetramanganese-oxo cubane complexes, their synthesis and their use as a functional catalyst for in vitro O₂ production. Preferred complexes are i) a tetramanganese-oxo cubane complex having the formula L₆Mn₄O₄, wherein Mn₄O₄, is a cubane core and L₆ are six facially-capping bidentate ligands bridging between the Mn atoms; ii) a manganese-oxo-pyramid complex having the formula L₆Mn₄O₃, wherein Mn₄O₃, is a pyramidal core and L₆ are six bidentate ligands bridging between the Mn atoms; and iii) a manganese-oxo-butterfly complex having the formula L₆Mn₄O₂ or L₅Mn₄O₂, wherein Mn₄O₂, is a butterfly core and L₆ or L₅ are six or five bidentate ligands bridging between the Mn atoms. Preferred ligands are carboxylate, phosphinate or diphenylphosphinate ligands. These catalysts may be used for the oxidation of water to oxygen and hydrogen peroxide and may also be used to catalyze the oxidation of chloride and simple chloride compounds to chlorine gas.

10 Claims, 10 Drawing Sheets

FIG. 1

CYCLE 1 — CYCLE 2

PROPOSED FOR PHOTOSYNTHESIS

COMPARISON OF ELECTROCHEMICAL POTENTIALS:

SCHEME 1. REACTION OF COMPLEX 1 WITH THE H ATOM DONOR, PHENOTHIAZINE

MN₄O₄-CUBANE TYPE CATALYSTS

CROSS REFERENCE TO RELATED APPLICATIONS

This is a divisional application of U.S. patent application Ser. No. 09/347,629 filed Jul. 2, 1999, now U.S. Pat. No. 6,316,653, the entire disclosure of which is expressly incorporated herein by reference.

This application claims the benefit of the filing date of U.S. Provisional Application Ser. No. 60/091,819, filed Jul. 6, 1998, and U.S. Provisional Application Serial No. 60/131,663, filed Apr. 29, 1999.

GOVERNMENT FUNDED RESEARCH

The present invention was supported by the National Institute of Health, and the government may have certain rights to this invention.

BACKGROUND OF THE INVENTION

1. Field of the Invention

This invention relates tetramanganese-oxo cubane complexes, their synthesis and their use as a functional catalyst for in vitro $O_2$ production. The compound of this invention has a cubical shaped core comprised of 4 Mn atoms and 4 O atoms and is supported by a surrounding matrix of six facially bridging chelates, preferably phosphinates ($RR'PO_2$), although other chelates are possible. The complexes of this invention are useful as catalysts for such industrially important reactions as the oxidation of chloride to chlorine, the oxidation of water to hydrogen peroxide and oxygen and oxygenation and oxidation reactions of hydrocarbons and organic substrates.

2. Related Art

The production of molecular oxygen by photosynthesis is a dominant global process that replenishes the atmospheric $O_2$ that is essential to sustain all aerobic life on earth. To date, until this invention, there does not exist a functional a functional catalyst for in vitro $O_2$ production. The use of such a catalyst for water oxidation would make available large quantities of oxygen needed to replace air for environmentally-clean fuel combustion and remote $O_2$ needs. The positive impact that such technology would have on improving health has global proportions for all respiring organisms, particularly those affected by respiratory diseases or dysfunctions.

More particularly, much of the industrialized world's air pollution comes from internal combustion engines, e.g., automobiles, trucks, diesal engines, etc. Such combustion engines produce $NO_x$ gases due to the use of air instead of pure oxygen for combustion. These gases are an essential causative agent in the formation of ozone, photochemical smog and atmospheric aerosols. Hospital visits for asthma and other respiratory disorders have been directly correlated with these pollutants. Ice core records from the South Pole indicate that $N_2O$ in the atmosphere has increased by 9% in the last 40 years (a much higher rate than in the previous 60 years), and continues to grow at an increasing rate.

Hydrogen peroxide, oxygen and chlorine are bulk chemicals used in large amounts in many industrial processes. For example, Chem. Engineering News, Jun. 23, 1997, p. 42, reported that in 1996, 355,000 tons of hydrogen peroxide (100%), 668,000 tons of oxygen, and 12,621,000 tons of chlorine were produced. Oxygen is currently obtained from air by separation using membranes and by liquification/distillation. Peroxide is made commercially by electrochemical reduction of oxygen catalyzed by quinones. It would be highly desirable to have a more economic means of producing such chemicals.

As indicated previously, there are no commercially viable man-made homogeneous catalysts for oxygen production by water oxidation. Such a commercially viable catalyst has many uses. For example, it could be used for the photochemical or electrochemical generation of $O_2$ from water to improve the efficiency of industrial combustion processes and automobile engines, while helping to solve a major air pollution problem.

It is known that photosynthetic oxygen evolution by water oxidation is catalyzed by a metalloenzyme that contains the same invariant inorganic core in all plants, comprised of a spin-coupled tetramanganese cluster, 1 $Ca^{2+}$ ion and an unknown number of Cl-ions. This water oxidizing complex (WOC) is an integral part of the Photosystem II (PSII) reaction center protein complex. The structure of the tetrameric Mn core has only been incompletely established, but has two Mn—Mn separations of 2.7 Å and 3.3 Å as seen by EXAFS. The WOC can be photooxidized by the PSII reaction center to produce five oxidation states, differing by one electron each and designated, $S_0, S_1, \ldots S_4$.

More particularly, the inorganic core of the photosynthetic water oxidase (WOC) is comprised of a cluster of composition $Mn_4O_xCa_1Cl_y$, in which only the stoichiometry of Mn and Ca are well established, Debus, R. J., Biochim. Biophys. Acta 1992, 1102, 269–352; Yachandra, V. K.; Souer, K.; Klein, M. P., Chem. Rev. 1996, 96, 2927–2950; Zaltsman, L.; Ananyev, G.; Bruntrager, E.; Dismukes, G. C., Biochemistry 1997, 36, 8914–8922; Ananyev, G. M.; Dismukes, G. C., Biochemistry 1997, 36, 11342–11350). Comparisons to Mn-oxo complexes have played a key role in suggesting possible core types such as the dimer-of-dimers, Yachandra, V. K., Sauer, K., Klein, M. P., Chem. Rev. 1996, 96, 2927–2950; Kirk, M. L., Chan, M. K., Armstrong, W. H., Solomon, E. I., J. Amer. Chem. Soc. 1992, 114, 10432–10440) $(Mn_2O_2)O(Mn_2O_2)^{n+}$, trigonal, Wang, S., Tsai, H. -L., Hagen, K. S., Hendrickson, D. N., Christou, G., J. Am. Chem. Soc. 1994, 116, 8376–8377) $Mn_4O_3X^{n+}$, distorted cubane, Vincent, J. B., Christou, G., Inorg. Chim. Acta 1987, 136, L41–L43; $Mn_4O_4n+$, adamantane Brudvig, G. W., Crabtree, R. H., Proc. Natl. Acad. Sci. USA 1986, 83m 4586–4588; Wieghardt, K., Angew. Chem. (Int. Ed. Engl.) 1989, 28, 1153–1172; $Mn_4O_6^{n+}$, and butterfly Vincent, J. B., Christou, G., Inorg. Chim. Acta 1987, 136, L41–L43) $Mn_4O_2^{n+}$.

Structurally characterized Mn compounds have been reported to catalyze water oxidation. For example, $Mn_6$-silesquioxane, is a hexanuclear cluster is a heterogeneous catalyst with low activity and stability. Another is a covalently-linked dimangano-porphrin complex that contains a biologically unavailable fluorinated ligand and is active for a few turnovers. Another compound is comprised of a demanganese-di-$\mu$-oxo core with terminal tridentate chelate (terpyridyl) and water, $Mn_2O_2$ $(terpy)_2(H_2O)$, Limburg. et al., (1999) Science, Vol. 283, 1524–1527. To date, no stab tetramanganese Mn complex of any type has been synthesized that exhibits four-electron redox chemistry, a hallmark of the WOC.

Multinuclear manganese-oxo clusters have been synthesized for use as molecular magnets, (Aubin, S. M. J.; Dilley, N. R.; Pardi, L.; Krzystek, J.; Wemple, M. W.; Brunel, L. -C.; Maple, M. B.; Christou, G.; Hendrickson, D. N., J. Am. Chem. Soc. 1998, 120, 4991–5004; Aubin, S. M. J.; Wemple, M. W.; Adams, D. M.; Tsai, H. -L.; Christou, G.;

Hendrickson, D. N., J.Am. Chem. Soc. 1996, 118, 7746–7754), oxidation catalysts, (Gardner, K. A.; Mayer, J. A., Science 1995, 269, 1849–1851) and bioinorganic compounds for photosynthetic water oxidation, (Brudvig, G. W.; Crabtree, R. H., Proc. Natl. Acad. Sci. USA 1986, 83, 4586–4588; Vincent, J. B., Christou, G., Inorg. Chim. Acta 1987, 136, L41–L43; Wieghardt, K., Angew. Chem. (Int. Ed. Engl.) 1989, 28, 1153–1172; Wieghardt, K., Angew Chemie, Int.Ed 1994, 33, 725–726. Christou, G., Acc. Chem. Res. 1989, 22, 328–335; Armstrong, W. In Manganese Redox Enzymes; V. L. Pecoraro, Ed., VCH: New York, 1992; pp 261–286; Pecoraro, V. L.; Baldwin, M. J.; Gelasco, A., Chem. Rev. 1994, 94, 807–826; Watkinson, M.; Whiting, A.; McAuliffe, C. A., J. Chem. Soc., Chem. Commun. 1994, 2141–2142).

The structure of the molecule of this invention was described by the inventors in a paper entitled Synthesis and Characterization of $Mn_1O_1L_6$ Complexes with Cubane-Like Core Structure: A New Class of Models of the Active site of the Photosynthetic Water Oxidase, W. Ruettinger, C. Campana, C. Dismukes (1997) J. American Chemical Society, Vol. 119, No. 28, pp. 6670–6671, July, 1997.

OBJECTS AND SUMMARY OF THE INVENTION

This invention is directed to novel, highly reactive, stable tetramanganese-oxo cubane complexes, their synthesis and their use as a functional catalyst for in vitro $O_2$ production. Preferred complexes are i) a tetramanganese-oxo cubane complex having the formula $L_6Mn_4O_4$, wherein $Mn_4O_4$, is a cubane core and $L_6$ are six facially-capping bidentate ligands bridging between the Mn atoms; ii) a manganese-oxo-pyramid complex having the formula $L_6Mn_4O_3$, wherein $Mn_4O_3$, is a pyramidal core and $L_6$ are six bidentate ligands bridging between the Mn atoms; and iii) a manganese-oxo-butterfly complex having the formula $L_6Mn_4O_2$ or $L_5Mn_4O_2$, wherein $Mn_4O_2$, is a butterfly core and $L_6$ or $L_5$ are six or five bidentate ligands bridging between the Mn atoms. Preferred ligands are carboxylate, phosphinate or diphenylphosphinate ligands.

A highly preferred complex of this invention has a cubical shaped core comprised of 4 Mn atoms and 4 O atoms and is supported by a surrounding matrix of six facially bridging chelates, preferably phosphinates ($RR'PO_2$), although other chelates are possible. This inorganic catalyst has been found to have a cubical core $(Mn_4O_4)(Mn_4O_4)$. Two distinct oxidation states have been found useful as catalysts, and include the "oxidized" member of the $Mn_4O_4$-Cubane family described in the aforementioned Synthesis and Characterization of $Mn_4O_4L_6$ Complexes with Cubane-Like Core Structure: A New Class of Models of the Active site of the Photosynthetic Water Oxidase, W. Ruettinger, C. Campana, C. Dismukes (1997) J. American Chemical Society, Vol. 119, No. 28, pp. 6670–6671, July, 1997 and Ruettinger. et al., (1999) Inorganic Chemistry, the entire disclosure of which is incorporated herein by reference.

These catalysts may be used for the oxidation of water to oxygen and hydrogen peroxide and may also be used to catalyze the oxidation of chloride and simple chloride compounds to chlorine gas. The catalysts are capable of both two-electron and four-electron oxidation reactions with or without dehydrogenation.

Additionally, due to the catalytic properties of these novel complexes they may be useful in fuel cell reactions, welding by, for example, automobile manufacturers, steel industry, chemical synthesis, pulp and paper bleaching, fertilizers, sewage treatment, bleaching applications, hospitals, bulk chemical commodities ($O_2$, $H_2O_2$, $Cl_2$), specialty chemical synthesis. These catalysts have characteristics similar to the photosynthetic enzyme which produces oxygen.

Synthesis of the cubical core is a two-step process having yields as high as 80% and comprises the ligand-assisted fusion of, for example, two $Mn_2O_2^{3+}$ cores. In order to enhance the commercialization prospects for these catalysts it is desirable to have a means to regenerate (reoxidize) these compounds.

BRIEF DESCRIPTION OF THE DRAWINGS

Other important objects and features of the invention will be apparent from the following detailed description of the invention taken in connection with the accompanying drawings in which:

FIG. 5A shows the electrospray ionization mass spectrum of a solution of a cubane core complex in trifluorosulfonic acid, and 5B shows 1 (60 μM) and 4 equivalents of PZH in $CH_2Cl_2/CH_3CN$ (1/4). The spectrum was recorded on a Hewlett Packard HP5989B; average of 1.5 to 4.2 min. spectral accumulation with $CH_3CN$ as the eluent; capillary voltage 25 V; ionization voltage 4 kV.

FIG. 11 shows the crystal structure of the inner core of $1^+$OTf · $CH_3CN$. In particular, the X-ray crystal structure (ORTEP plot with 50% probability level) of $1^+$OTf (phenyls and counter ion omitted for clarity). Selected bond lengths (Å) and angles (degree°): Mn(1)-Mn(4) 2.9038(4); Mn(1)-Mn(2) 2.9826(4); Mn(1)-Mn(3) 2.9126(4); Mn(2)-Mn(4) 2.8341(4); Mn(3)-Mn(4) 2.8588(4); Mn(2)-Mn(3) 2.8377(4); Mn(1)-O(1) 2.049(2); Mn(1)-O(2) 1.9233(14); Mn(1)-O(3) 2.040(2); Mn(2)-O(1) 1.8923(14); Mn(2)-O(3) 1.905(2); Mn(2)-O(4) 1.9151(14); O(1)-Mn(1)-O(2) 79.35(6); O(1)-Mn(1)-O(3) 77.58(6); O(1)-Mn(2)-O(3) 84.84(7).

DETAILED DESCRIPTION OF THE INVENTION

The preferred cubical shaped molecule of this invention comprises 4 Mn atoms and 4 O atoms supported by a surrounding matrix of phosphinates ($RR'PO_2$). These manganese-oxo containing cubane-shaped or butterfly-shaped complexes are useful as catalysts for the reactions described herein. It is believed that during a catalytic reaction the cubane-shaped molecules undergo a structural rearrangement to form butterfly-shaped molecules:

$L_6Mn_4O_4$, $[L_6Mn_4O_4]^+X^-$  Cubanes $L_6Mn_4O_2$, $[L_6Mn_4O_2]^{2+}(X^-)_2$  Butterflies Wherein:
$X^-$ is any mono anion that is non-coordinating, e.g., $ce^-$, triflate, etc.
L is $RR'PO_2^+$ phosphinate, $(RO)(RO')PO_2^-$ phosphate diesters, diphenylphosphinate, $RR'R''CO_2^-$ carboxylate ligands.

The cubane shaped molecule of this invention was synthesized to partially mimic the active site of the enzyme found in green plants which produce oxygen by the oxidation of water during photosynthesis. Synthesis of the cubical core involves a two step synthesis typically at 30% yields, however 60–85% yields have been obtained.

A preferred "cubane complex" $Mn_4O_4(O_2P(Ph)_2)_6$, wherein $O_2P(Ph)_2^-$ is diphenylphosphinate, has been synthesized and structurally characterized. The complex molecule contains an example of an all oxo $Mn_4O_4$ cubane core. Previous theories have suggested that this core may be part of the catalytic site for photosynthetic water oxidation in vivo.

The cubane core complex was synthesized by ligand-assisted fusion of two $Mn_2O_2^{3+}$ cores. The structure was established by single-crystal X-ray diffraction. The lattice belongs to the cubic crystal system with a=b=c=30.223(2) Å and crystallizes in the space group $P2_13$.

Each unit cell contains four independent molecules with bond distances and angles differing only slightly, principally in the orientation of the phenyl rings, which may be due to packing effects. Each molecule exhibits crystallographic $C_3^{-3}$ symmetry, but the $Mn_4O_4$ core is nearly tetrahedral. The differences in the Mn—Mn distances are quite small with an average separation of 2.926±0.022 Å.

The oxidation states of the manganese ions are formally 2 III and 2 IV based on the charge balance. The valence electrons appear to be delocalized with no substantial Jahn-Teller distortions, yielding a rare example of a class III (delocalized) mixed valence $Mn^{III}Mn^{IV}$ complex. This interpretation is supported by solution H NMR studies showing only one set of paramagnetically shifted resonances for the three phenyl ring protons from all ligands.

The electronic absorption spectrum of the cubane core complex in $CH_2Cl_2$ exhibits multiple bands at 498 mn ($\epsilon 1.4\times 10^3$ $M^{-1}cm^{-1}$), 697 nm ($\epsilon = 1.4\times 10^2 M^{-1}cm^{-1}$) and several overlapping bands in the near-IR region between 800 and 1100 nm ($1.2\times 10^2$ $M^{-1}cm^{-1}$) that are found in $\mu$-oxo-bridged dimanganese (III,IV) complexes. In contrast to these $Mn_2O_2^{3+}$ core complexes, the cubane cluster is EPR silent between 10° K and 230° K, indicative of electronic coupling.

Cyclic voltammetry in dichloromethane reveals a quasi-reversible one-electron oxidation process ($E_{1/2}=680$ mV vs. ferrocene) and an irreversible multi-electron reduction process ($E_c=-730$ mV; cathodic peak potential).

Irreversible multi-electron reduction of the $Mn_4O_4^{6+}$ "cubane" core complex, $Mn_4O_4L_6$ (1) (L=diphenylphosphinate) occurs in solution using one-electron reductants like cobaltocene or electrochemical reduction at potentials below $-0.1$ V (vs. NHE) with release of free Mn(II). By contrast, reduction with the hydrogen atom donor, phenothiazine, forms 4 equivalents of the neutral phenothiazine radical and an EPR-silent intact $Mn_4$ cluster, 2.

Electrospray mass spectrometry of 2 indicates the loss of two bridging oxygen atoms from the cubane core complex, establishing formation of $Mn_4O_2L_6$ exhibiting the $Mn_4O_2^{6+}$ "butterfly"core. Thus, the cubane core complex undergoes coupled four-electron/four-proton reduction with release of two water molecules, a reaction formally analogous to the reverse sequence of steps in photosynthetic water oxidation.

Figure 1:
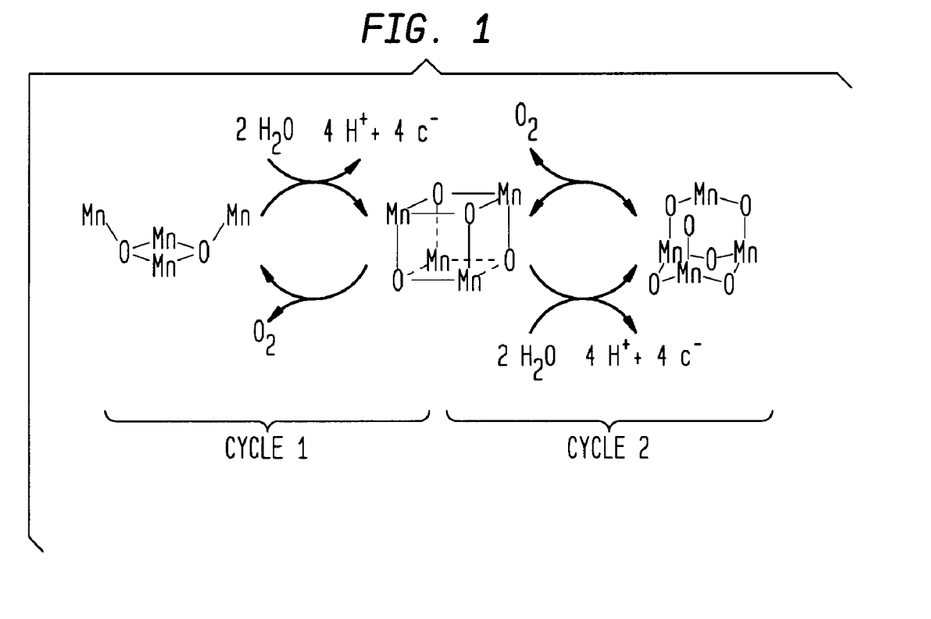
FIG. 1 is a schematic of a proposed mechanism for water oxidation by photosynthetic water oxidase complex (WOC) of PSII.

Referring to FIG. 1, it has been postulated that the oxo-manganese cubane core structure, $[Mn_4O_4]^{x+}$ is part of the catalytic cycle for dioxygen production by the photosynthetic water oxidizing complex (WOC) through two independent hypotheses. The oxo-manganese cubane core structure, $[Mn_4O_4]^{x+}$, is particularly interesting because it has not been previously isolated as a discrete complex.

More specifically, still referring to FIG. 1, in one proposal, oxide ions from water are incorporated into a butterfly-type core, $Mn_4O_2$, resulting in the formation of an "activated" cubane core which releases dioxygen with regeneration of the butterfly core. This proposal was based on the established structure of several butterfly core complexes but lacked evidence for oxidation to a cubane core. In a second proposal, oxide ions from water are added to a cubane core forming an "activated" $Mn_4O_6$-adamantane core which in turn eliminates dioxygen and reverts to the cubane. This proposal was based on the established adamantane structure of the $Mn_4O_6$ core. Neither of these proposed reactions has been experimentally demonstrated.

EXAMPLES

Synthesis of the $Mn_4O_4$ Cubane Core

Prior to this invention the $Mn_4O_4$ cubane core has not been synthesized. One method of synthesizing $Mn_4O_4(O_2P(Ph)_2)_6$, the cubane core complex, was done by fusing together two pre-formed $Mn_2O_2^{3+}$ units. A dimerization approach was previously successful for the synthesis of a $Co_4O_4$ cubane complex starting from a complex with a dimeric $Co^{III}_2(OH)_2$ core and using bidentate ligands with shorter bridging atom separation. The cubane core complex forms after addition of diphenylphosphinate salts to a solution of $[Mn_2O_2(bpy)_4](ClO_4)_3]$ in acetonitrile.

Another synthetic route to produce the complex cubane, $Mn_4O_4(O_2P(Ph)_2)_6$ appears to appears to be generalizable to other chelates or ligands (L) other than phosphinates. Through this process it is possible to eliminate the initial step in the foregoing process involving isolation of the mixed-valence dimeric intermediate, $Mn_2O_2^{3+}[Mn_2O_2(bpy)4]^{3+}$. The is process is a two-step one-pot reaction in which a simple manganese salt of diphenylphospinate, Mn(O2PPh2)2, is first synthesized via a modification of a procedure described in Betz et al., "Polymeric and Monmeric Forms of Metalphosphinates." *Inorg. Chim. Acta*, 1988, 147, 109–113, the entire disclosure of which is incorporated herein by reference.

The initial yield from two trials indicates yields are greater than 50%. This process has been used to synthesize a new cubane derivative having bis(para-methylphenyl) phosphinate as the facially bridging chelates (L). This method may be extendable to the synthesis of derivatives of $Mn_4O_4$-cubanes with non-phosphinate chlelates (L), such as dicarboxylates, phosphate diesters, among others.

Characterization of the Cubane Core Complex

The IR spectrum of the cubane core complex shows mainly vibrations due to the phosphinate group and confirms the absence of perchlorate counterions or bpy ligands. MALDI-TOF mass spectral data indicate an apparent molecular mass of 1583–1584 D, corresponding to the formulation $Mn_4O_4L_6$ (1586.7 D), which is also supported by elemental analysis.

Figure 2:
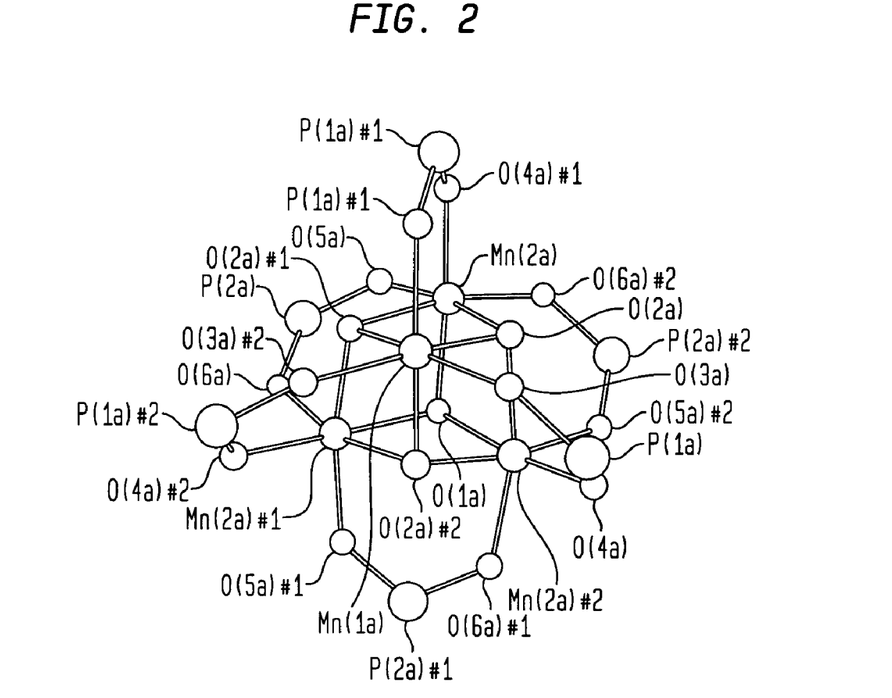
FIG. 2 shows the structure of the cubane core complex as determined by X-ray diffraction together with selected bond distances and angles. The plot is a thermal ellipsoid plot (50% probability) of one of four molecules in the unit cell of the catalyst of this invention. The phenyl groups are omitted for clarity. The selected bonded distances (Å) and angles (deg.) are as follows: Mn(1a)-Mn(2a), 2.914(3); Mn(2a)-Mn(2a)#1, 2.949(3); Mn(1a)-O(2a), 1.917(7); Mn(1a)-O(3a)#1, 1.951(8); Mn(2a)-O(1a), 1.982(7); Mn(2a)-O(2a), 1.882; Mn(2a)-O(4a)#1, 1.955(9); O(2a)-Mn(1a)-O(2a)#1, 82.3(3); O(1a)-Mn(2a)-O(2a), 84.3(3), O(2a)-Mn(2a)-O(2a)#1, 80.8(3).

FIG. 2 shows the structure of the cubane core complex as determined by X-ray diffraction together with selected bond distances and angles. The molecule shown is one of the four independent molecules in each unit cell with slightly different bond distances and angles. The molecules differ mainly in the orientation of the phenyl rings, probably due to packing effects. Diphenylphosphinate ligands bridge between Mn pairs across each of the six $Mn_2O_2$ faces of the cube. This feature distinguishes the cubane core complex from the more compact $Co_4O_4$ cubane which has two μ-bridging acetates on opposite faces, and the pseudo-cubanes, $Mn_4O_3X$, which have three faces bridged by carboxylates ($Mn^{IV}$–$Mn^{III}$, 2.8 Å) and three open faces ($M^{III}$–$Mn^{III}$, 3.2–3.3 Å). Each independent cluster of the cubane core complex contains one unique and three symmetry-related Mn ions. No large (Jahn-Teller) distortions are observed in the Mn-O bond lengths, and this absence appears not to be due to a superposition of inequivalent Mn valences. Further support comes from the absence of appreciable differences in the anisotropic displacement factors for different O atoms, unlike the mixed valence complex $Mn_2O_2phen_4^{3+}$, where these are 5–8 times large for the axial metal ligand bonds. These features suggest that the valence electrons may be delocalized, yielding a rare example of a class III (delocalized) mixed-valence $Mn^{III}M$-$n^{IV}$ compound. This conclusion is supported by variable temperature $^1H$ NMR spectra of the cubane core complex, showing that even in solution only one set of three para-magnetically shifted resonances for all 12 phenyl rings are observable.

The Mn—Mn distances in the cubane core complex vary between 2.904 Å and 2.954 Å in the four independent molecules (average for all Mn—Mn distances in all four independent molecules is 2.926 Å). The Mn—Mn distances are considerably longer than observed for both the di-μ2-oxo bridged dimers (2.6–2.7 Å),$^i$ as well as the tri-μ2-oxo bridged Mn(IV) dimer (2.296 Å), both of which contain μ2-bridging oxo ligands. The Mn—Mn distances are comparable to the $Mn(IV)_4$ cubanes embedded within the larger clusters of $Mn_{12}O_{12}$ and $Mn_8Fe_4O_{12}$ (2.82–2.99 Å), and to the central pair in the $Mn_4O_2$-butterfly complexes (2.85 Å) FIG. 1, left), both of which contain exclusively triply-bridging μ3-oxos.

The distorted cubane core in $Mn_4O_3X$ also contains exclusively μ3-oxo bridges. Here the Mn—Mn separations are either slightly shorter (2.8 Å) across the faces of $Mn_2O_2$ rhombohedra that are bridged by carboxylate, or much longer (3.3 Å) across unbridged faces of $Mn_2OCl$ rhombohedra. From this comparison we propose that the core expansion by 0.2–0.3 Å observed upon fusion of two $Mn_2(μ2-O)_2$ rhombohedra to form the $Mn_4(μ3-O)4$ cubane is promoted by coordination of the six μ-bridging phosphinates, while carboxylates do not stabilize this expansion. The O,O distance in diphenylphosphinic acid is 2.58 Å whereas the O,O distance is acetic acid is only 2.22 Å. These distances change only slightly (<1%) upon coordination in μ-bridging phosphinate or acetate complexes.

The complex exhibits several electronic transitions at: (λmax (nm), εmax ($M^{-1}cm^{-1}$)) 498 (1.4×$10^{-3}$), 697 (1.4× $10^2$), and overlapping bands between 800 and 1100 (1.2× $10^2$). The latter bands bleach upon partial reduction by two H atoms using phenothiazine, suggesting assignment as Mn inter-valance electronic transitions. However, contributions from oxo-to-Mn charge transfer reactions are possible as well. The complex is EPR silent in $CH_2Cl_2$ solution between 10° K and room temperature, indicating magnetic coupling within the tetramer.

The cyclic voltammogram of the cubane core complex in dichloromethane exhibits a quasi-reversible oxidation at $E_{1/2}$=+680 mV vs. ferrocene (Fc); estimated +1.38 V vs. NHE. The ratio of peak currents for $Fc^+/Fc$ and $1^+/1$ equals 1.2±0.05 at scan-rates between 5 and 50 mV/sec. The peak-to-peak separations are slightly larger for the complex compared to Fc, but the ratio of the values remains constant at 0.7±0.06. The deviation from the ideal values of 1.0 for the ratio of peak currents and the peak-to-peak separation might reflect the difference in the diffusion coefficients for the two compounds and cannot be accounted for by a two-electron process for the complex. The oxidation product is EPR active. Accordingly, the oxidative process at +680 mV is assigned to a quasi-reversible one-electron oxidation (2III, 2IV)⇌(III, 3IV). The complex $^+$ exhibits a considerable more positive reduction potential by 0.7 to 1.7 V than found for dimanganese (III,IV)/(III,III) couples and greater than the majority of known (IV,IV)/(III,IV) couples of dimeric $Mn_2O_2$ complexes.

The cubane core complex also exhibits an irreversible reduction process at an anodic peak potential of −730 mV vs. Fc in dichloromethane (at a scan-rate of 50 mV/sec; peak-to-peak separation of 700–800 mV). Titration of the cubane core complex with phenothiazine, monitored by the electronic absorption band of the phenothiazine neutral radical at 380 nm and its EPR spectrum, reveals that a total of 4–5 H atoms are taken up upon reduction of the cubane core complex without decomposition to monomeric Mn(II). The stoichiometry suggests formation of the tetrakis-μ-hydroxo cubane core, $Mn_4(OH)_4L_6$.

Figure 3:
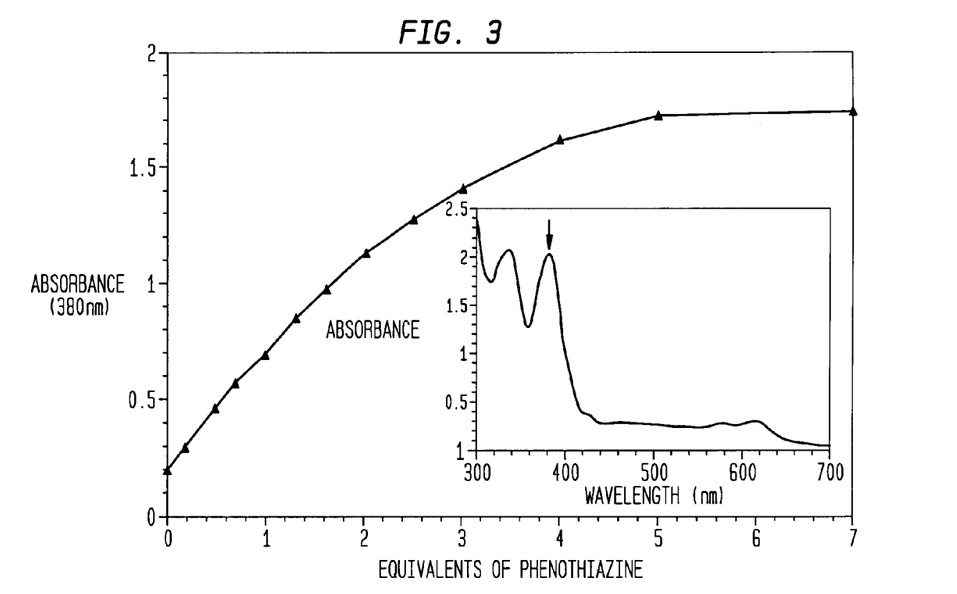
FIG. 3 shows absorption change at 380 nm (λmax of the neutral PZ radical) during the titration of 0.05 mM 1 with phenothiazine (PZH). The inset shows the UV-VIS spectrum of the reaction mixture containing 0.2 mM 1 and 2 eq. PZH.
Figure 6:
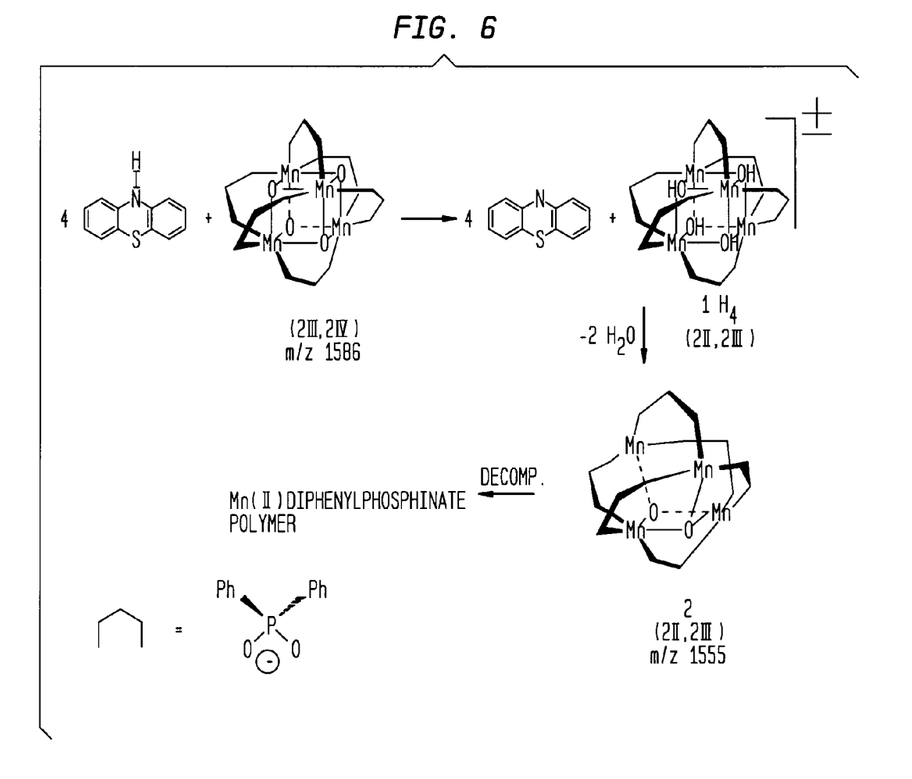
FIG. 6 is a proposed reaction using the novel catalyst of this invention showing reduction of the oxos to water molecules.

FIG. 6 depicts the reaction of the cubane core complex, $Mn_4O_4L_6$ in $CH_2Cl_2$ with phenothiazine (PZH). The reaction generates the neutral PZ radical (loss of H atom) which, referring to FIG. 3, reaches an endpoint between 4 (94%) and 5 (100%) equivalents, quantitated by its UV-VIS spectrum.

Figure 4:
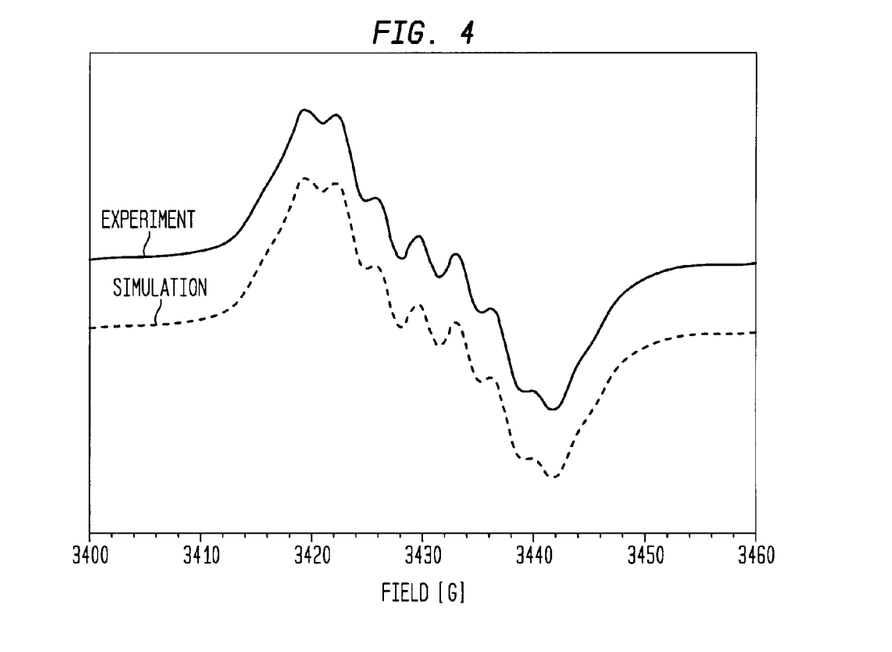
FIG. 4 the solid line shows the EPR spectrum (9.4 Ghz, mod. freq. 100 kHz, mod. amp. 0.1 G) of the PZ neutral radical at room temperature after addition of 4 eq. of PZH to a 0.2 mH solution of the cubane core complex. The dashed line shows a spectral simulation using the published H hyperfine parameters. neutral radical: N(7.06 G), $H_{1,2}$ (2.68 g), $H_{3,4}$(1.00 G), $H_{5,6}$(3.64 G), $H_{7,8}$(0.73 G); linewidth 2.0 G.

Referring to FIG. 4, the exclusive formation of the neutral PZ radical by oxidation of PZH was confirmed by spectral simulation of its EPR signal detected in reaction mixtures. The unusual stability of the radical in reaction mixtures (no decay was observed within minutes) may be attributed to the formation of a complex between 2 (FIG. 6) and PZ.; which is also confirmed by the fact that the EPR signal of the radical cannot be microwave power saturated even at 10 K. The reduction product of the cubane core complex, $Mn_4O_4L_6$ is an EPR-silent (7–30 K, 150 K) intact $Mn_4$ cluster 2. Excess PZH (up to 10 equivalents) does not further reduce 2 or release free Mn(II). No intermediates in the reduction can be observed by EPR spectroscopy using sub-stoichiometric amounts of reductant. $^1$H-NMR spectroscopy reveals that at room temperature, none of the six ligands (L) dissociate from 2 and the product exhibits greater line broadening than the cubane core complex, $Mn_4O_4L_6$, indicative of enhanced paramagnetism and weaker electronic exchange coupling compared to the cubane core complex, $Mn_4O_4L_6$. Hence, the reaction constitutes a concerted transfer of four H-atoms to the cubane core complex, $Mn_4O_4L_6$.

Figure 5:
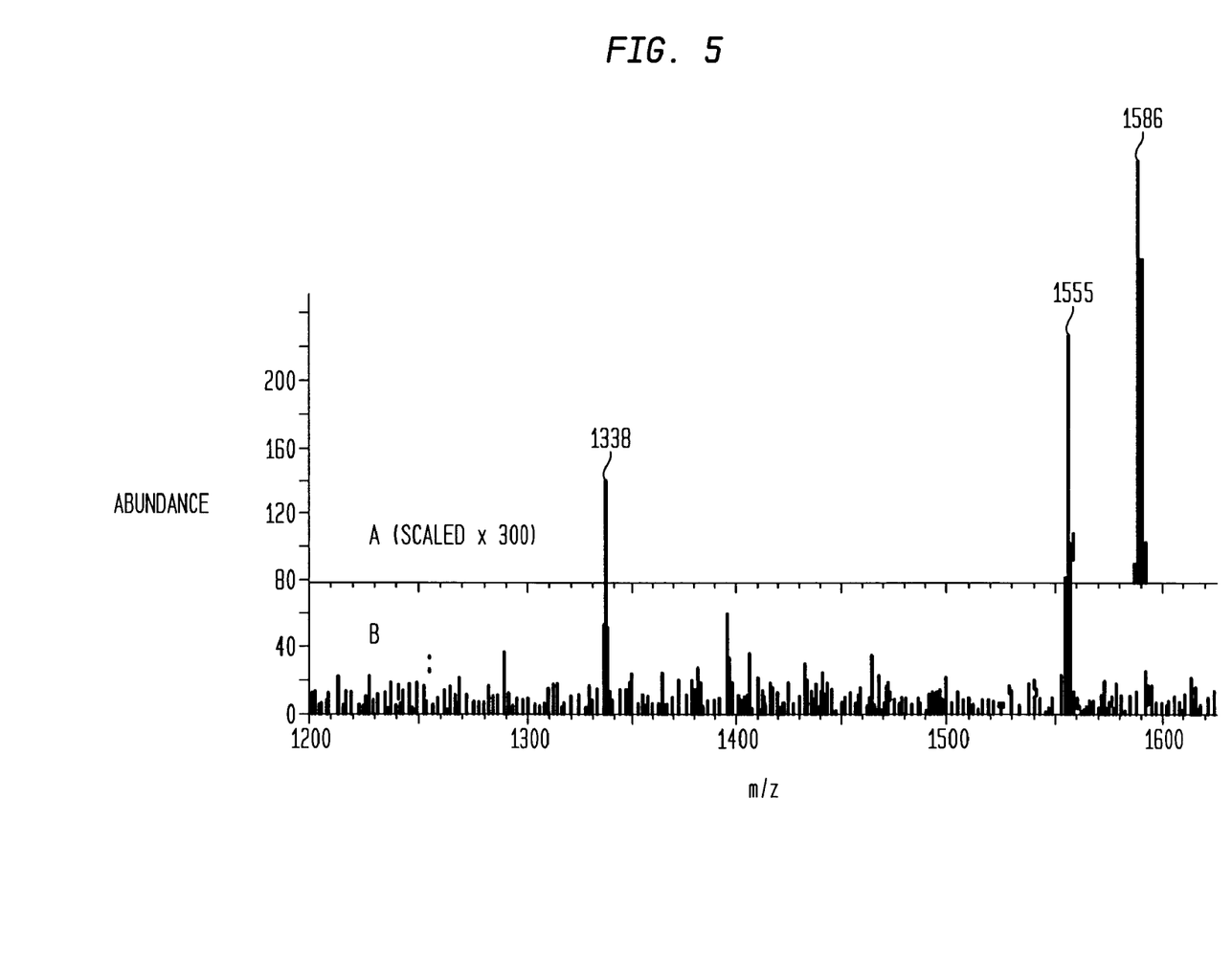

Electrospray ionization mass spectrometry (ESI-MS) has proven to be a useful method in the detection of oxo-bridged Mn complexes. ESI-MS of the cubane core complex, $Mn_4O_4L_6$ in trifluorosulfonic acid yields a parent ion cation peak of 1588 (m/z, 1H$^+$, FIG. 5A), in agreement with previous MALDI-TOF-MS for the unprotonated cubane core complex, $Mn_4O_4L_6$. ESI-MS data of the PZH reduction product 2 (FIG. 5B) shows complete loss of peaks for the cubane core complex, $Mn_4O_4L6$ and the appearance of peaks for the species 1–32 (m/z 1555) and 1-L-32 (m/z 1337), consistent with the removal of two bridging oxo ions as water molecules from the cubane core (FIG. 6). Since the hydrogenated complex 2 is formally uncharged, either protonation or one-electron oxidation under ESI measurement conditions must lead to the detected single positively charged complex (2, m/z 1555), whereas loss of diphenylphosphinate from 2 leads to detection of (2-L, m/z 1337).

Attempted isolation of 2 as a crystalline solid has so far failed. Mass (MALDI-TOF) and infrared spectral data of material isolated from reaction mixtures after solvent evaporation show that the cubane core is not present, but instead a Mn(II)diphenylphosphinate polymer is isolated whose IR-spectrum is closely analogous to a homogeneous solid Mn(II)diphenylphosphinate polymer obtained independently. We therefore conclude that the proposed initial reduction product of the cubane core complex, $Mn_4O_4L_6$, namely $1H_4$ (FIG. 6) loses two water molecules to form the species $[Mn_4O_2L_6]$ (2) with a formal mixed valence (2II, 2III) tetranuclear manganese core seen in mass spectra. Loss of water from $1H_4$ would be compatible with the unusually long (i.e., weak) Mn—O(oxo) bonds in the cubane core complex, $Mn_4O_4L_6$. Although the structure of this species is unknown, it most likely corresponds to a butterfly-type core analogous to that formulated in FIG. 6, in which all phosphinate ligands remain bound as bridging chelates and two oxos are removed. This species contains coordinatively unsaturated Mn(II) and Mn(III) ions and should be unstable toward oligomerization. Indeed, attempted isolation leads to decomposition to a Mn(II) polymer.

Two $Mn_4O_2^{6+}$ butterfly structures with a mixed valence Mn(2II,2III) core have been previously synthesized using carboxylate ligands and found to possess a nearly planar $Mn_4O_2$ core. Both were stated to be EPR-active (unlike 2) with an S=2 ground state and low-lying excited spin states as determined by magnetic susceptibility studies. No further analysis of the EPR spectra were reported. This difference in EPR properties suggests the possibility of a non-planar core geometry for 2.

The chemistry in FIG. 6 constitutes the first example of a concerted four-electron plus four-proton transfer process involving interconversion between stable Mn clusters. This chemistry leads to the release of two water molecules, a reaction formally analogous to the reverse sequence of steps that occur leading up to photosynthetic $O_2$ evolution. The "cubane-butterfly" core conversion, 1→2, is also equivalent to a model proposed for the structural rearrangement that triggers $O_2$release during the final step of photosynthetic water oxidation, $S_3→S_4^*→S_0+O_2$. Functional modelling of the $O_2$ evolution step starting from 1 has not been observed to date, and thus may require surmounting an additional activation barrier and/or further oxidation.

The novel catalyst molecules of this invention include three distinct structural families of molecules: (1) the manganese-oxo-cubanes, (2) the manganese-oxo-pyramids, and (3) the manganese-oxo-butterflies.

(1) The manganese-oxo-cubanes are represented by the formula $L6Mn_4O_4$ all containing the cubane structure core, $Mn_4O_4$, and six facially-capping bidentate ligands (L) of specified type that bridge between Mn atoms.

(2) The manganese-oxo-pyramids are represented by the formula $L6Mn_4O_3$, all containing the pyramidal core, $Mn_4O_3$, and six bidentate ligands (L) of specified type that bridge between Mn atoms.

(3) The manganese-oxo-butterflies are represented by the formula $L_6Mn_4O_2$ and $L_5Mn_4O_2$, all containing the butterfly core, $Mn_4O_2$, and six or five bidentate ligands (L) of specified type that bridge between Mn atoms.

The manganese-oxo-cubanes (1) can be converted to the manganese-oxo-pyramids (2) with transfer of oxo or hydroxo into substrate depending on the starting oxidation state of the cubane. The manganese-oxo-cubanes (1) can be converted to the manganese-oxo-butterflies (3) with transfer of 2 oxos or 2 hydroxo into substrate depending on the starting oxidation state of the cubane. The cubane, pyramid and butterfly structures can be interconverted using either $O_2$ or electrochemical transformation in the presence of water.

The manganese-oxo cubanes (1) are well suited to oxo-transfer and hydroxylation reactions of organic precursors, as well as two-electron oxidations to produce important commodity chemicals. There are potentially many applications possible, including chirally selective catalysis using appropriate ligands (L).

The demonstrated transformations of the manganese-oxo cubanes include:

1. Phosphines to phospine oxides: $R_3P→R_3P$-O
2. Amines to amine oxides: $R_3N→R_3N$-O
3. Phenols to quinones: Ar-OH→Ar(OH)$_2$ →O=Ar=O
4. Thioethers to sulfoxides: R—S—R →R—S(O)—R
5 Alkenesto epoxides:

6. Water to hydrogen peroxide $2 H_2O \rightarrow HOOH + 2e^- + 2 H^+$
7. Chloride to chlorine: $2 Cl^{31} \rightarrow Cl_2$
8. As yet uncharacterized products are formed with alkanes, alkynes and aromatics.

Figure 7:
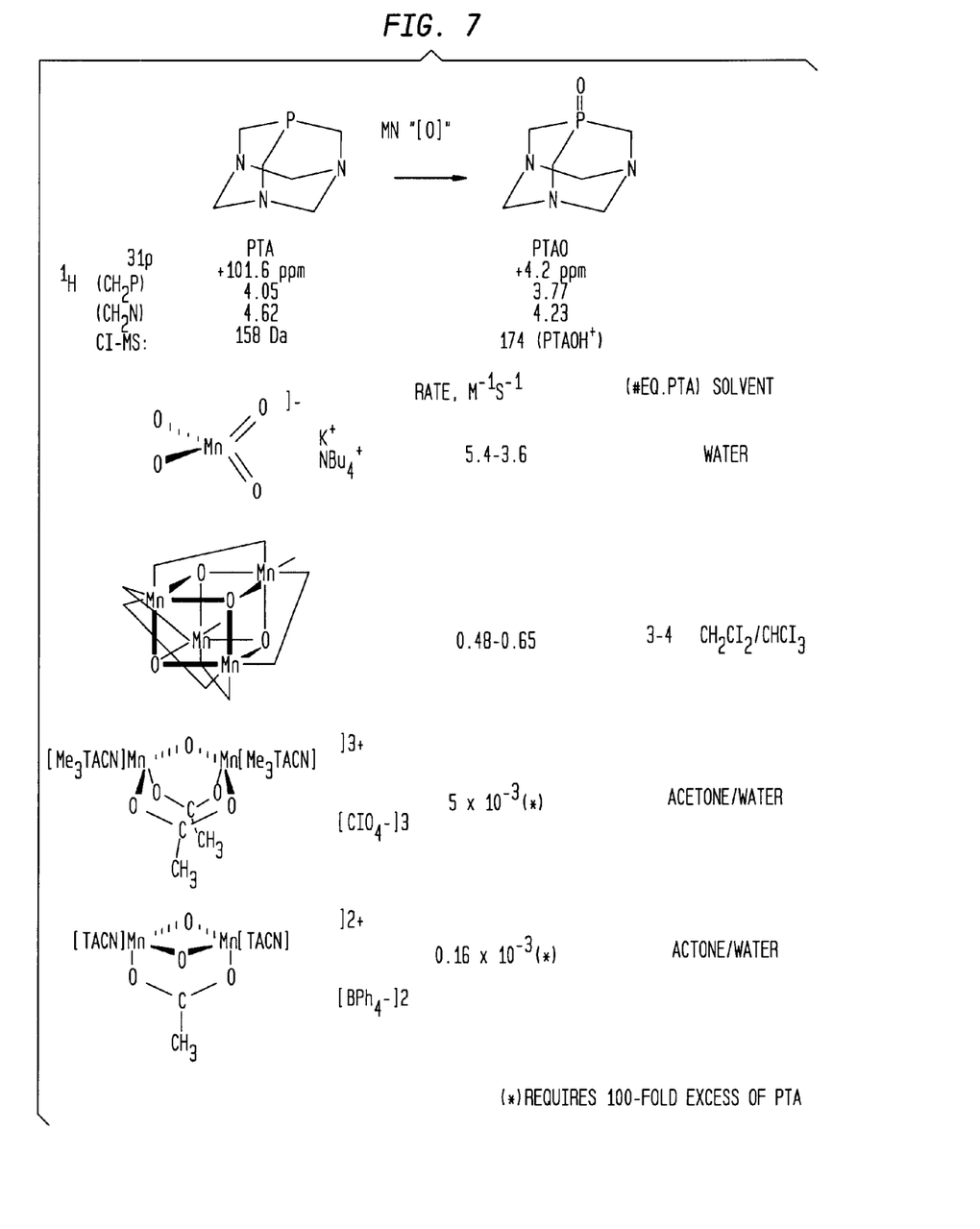
FIG. 7 is a diagram of chemical reaction rates for oxygen atom transfer to phosphine (PTA) by the manganese oxo cubane of this invention compared to other manganese-oxo complexes.

FIG. 7 shows chemical reaction rates for oxygen atom transfer to phosphine (PTA) by the manganese oxo cubane compared to other manganese-oxo complexes. The oxo atoms react at high rates comparable to permangante.

Figure 8:
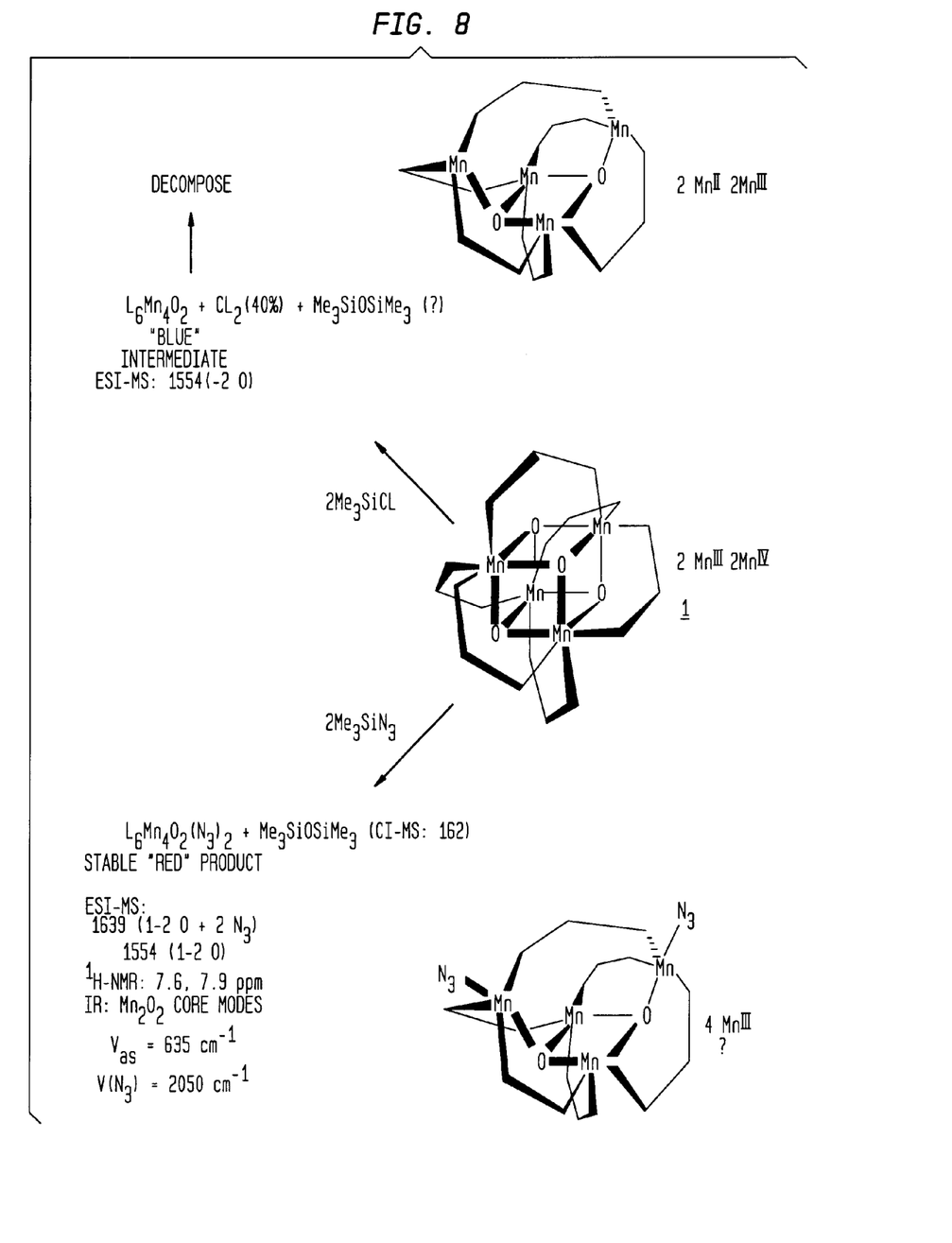
FIG. 8 schematically depicts the manganese-oxo cubane reacting with deoxygenating reagents ($Me_3Si$-X, X=Cl or $N_3$) by removing two oxygen atoms from the cubane to form the "butterfly" core $Mn_4O_2$ compound and the ether $Me_3SiOSiMe_3$.

FIG. 8 shows the reaction of manganes-oxo cubane with deoxygenating reagents ($Me_3Si-X$, $X=Cl$ or $N_3$) by removing two oxygen atoms from the cubane to form the "butterfly" core $Mn_4O_2$ compound and the ether $Me_3SiOSiMe_3$. In the case of $Me_3SiCl$, the manganese intermediate ($Mn_4O_2Cl_2$) rearranges to form $Cl_2$ in 40% yield.

Comparison of The Structure of the $Mn_4Ca_1$ Core of the PSII Water Oxidizing Complex (WOC) and the $Mn_4O_4$-Cubane/$Mn_4O_2$-Butterfly Model Complexes Multiline EPR from a Cuboidal $Mn_4O_4$ Core.

Figure 9:
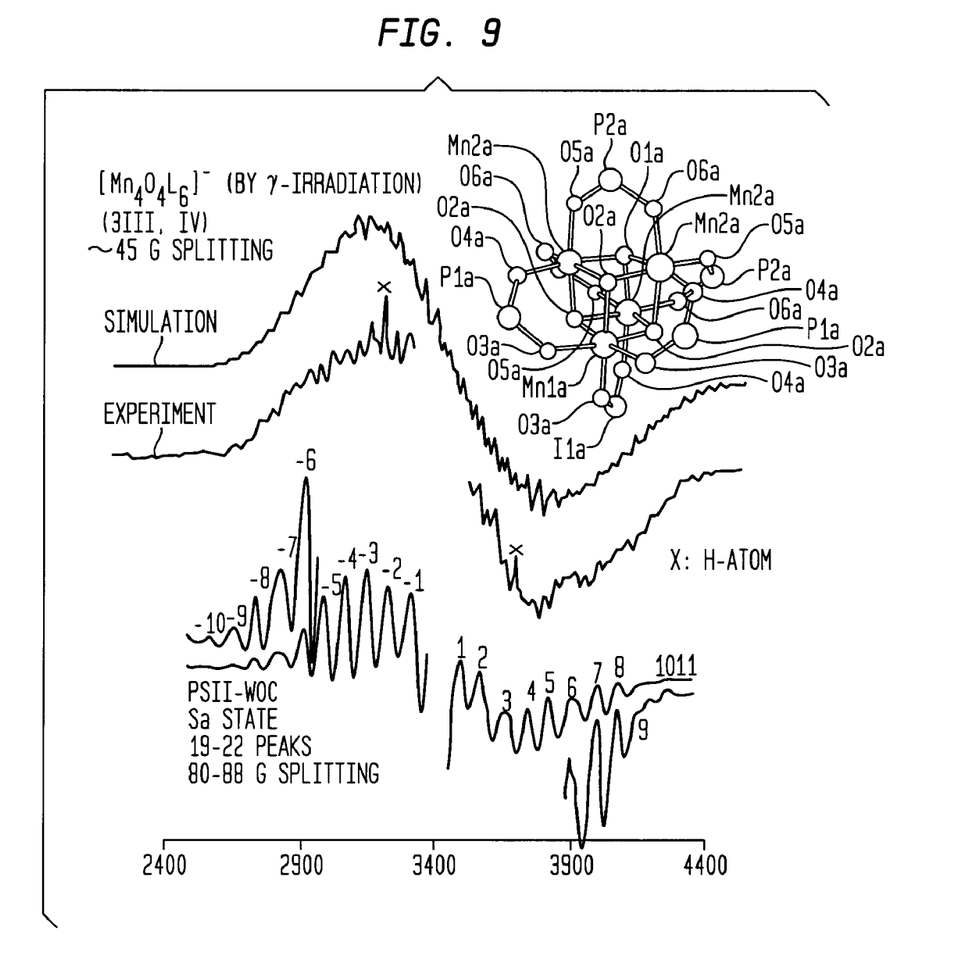
FIG. 9 is an X-band EPR spectrum at 6 K of cubane 1 in $CH_2Cl_2$/ 30% MTHF after γ-irradiation (1 Mrad at 77 K) compared to the $S_2$ state multiline signal of the native WOC-PSII enzyme (bottom trace). (Zheng, M.; Dismukes, G. C., Inorganic Chemistry 1996, 35, 3307–3319)
Figure 10:
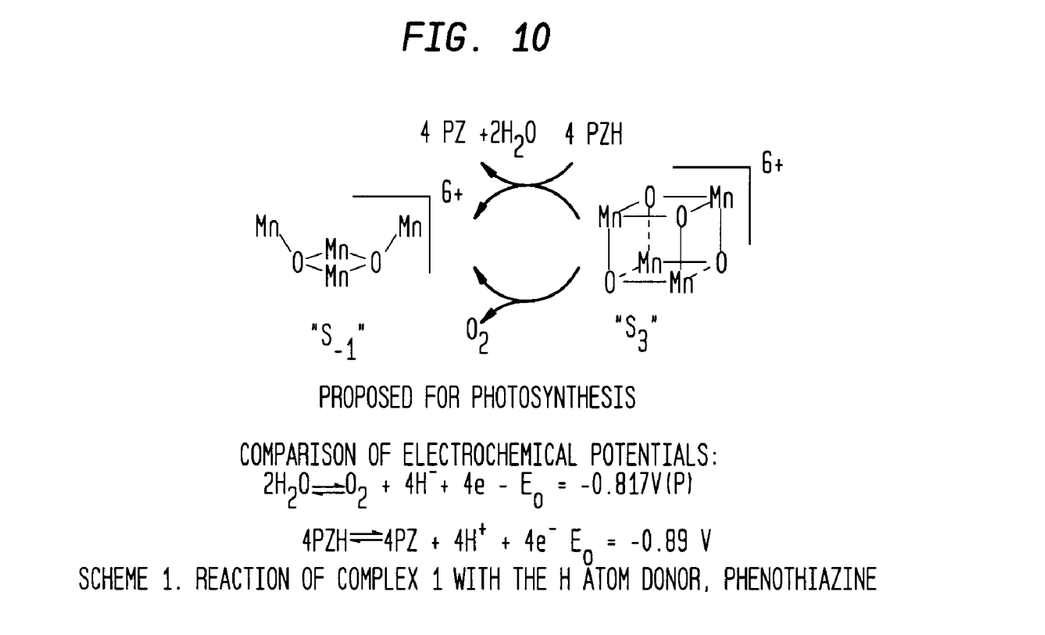
FIG. 10 depicts the reaction of complex 1 with the H atom donor, phenothiazine.

In FIG. 9, the EPR spectrum of the first example of a cuboidal $[Mn_4O_4]^{5+}$ cluster shows that this core geometry produces a doublet ground state having the same class of multiline hyperfine structure as seen for the $S_2$ state of the WOC. The paramagnetic molecule $L_6Mn_4O_4-(1^-)$, was produced by gamma irradiation of the symmetrical "cubane" core complex, $L_6Mn_4O_4$ (1), $L^{31}$=diphenylphosphinato$^-$. (R üttinger, W.; Campana, C.; Dismukes, G. C., J. Amer. Chem. Soc. 1997, 119, 6670–6671) This multiline EPR signal exhibits virtually identical total spin density on the four Mn ions (spectral breadth) as found in the $S_2$ oxidation state of the WOC, but has a different distribution of spin densities among the Mn ions. The ratio of Mn spin densities predicted by the X-band EPR simulation suggests that the unpaired spin densities are distributed asymmetrically with approximate relative magnitudes of 1, 1.1, 1.7 and 2.4 (preliminary). The distribution indicates that upon 1 $e^-$ reduction the nearly symmetrical core complex 1 undergoes a distortion in which two of the Mn ions carry more spin density than the remaining two.

Oxidation of 1 electrochemically or by $O_2$ in the presence of triflurosulfonic acid (HOTf) or trimethysilytriflate ($Me_3SiOTf$) was found to form the one-electron oxidized cubane, $1^+$. The electrochemical potential for this reversible process is 1.4 V (NHE). The crystal structure of $1^+OTf.CH_3CN$ (FIG. 11) was obtained and reveals significant trigonal contraction around Mn, compared to the symmetrical core of 1. There are two types of Mn—Mn distances averaging 2.93 Å ($Mn^{III}$–$Mn^{IV}$) and 2.84 Å ($Mn^{IV}$–$Mn^{IV}$). The trigonal distortion indicates that electronic localization occurs. However, no obvious Jahn-Teller distortion is seen for $Mn_1^{(III)}$ as evidenced by the $Mn_1$-O bond lengths (avg. $Mn_1$-O(oxo) 2.004 Å; $Mn_1$-O(phos) 1.939 Å). The X-band EPR spectrum of a solution of $1^+$ in acetonitrile (FIG. 9) indicates that $1^+$ has a high-spin ground state with $S=3/2$, consistent with the formal Mn oxidation states III,3IV. A multiline signal is not observed.

In summary, the multiline EPR spectra of the $S_2$ state of the WOC and the cubane model complex $1^-$ indicate that the $Mn_4$ core of the WOC is not an open dimer-of-dimers structure, but is compatible with a cuboidal cluster or bent butterfly cluster with $C_{2v}$- symmetry. Also, the Mn oxidation states of the $S_2$ state are best described as 3III,IV.

Modelling of Water Oxidation via Cubane-Butterfly Core Conversion.

Reductive titration of 1 using the H-atom donor phenothiazine (PZH) was monitored by UV spectrophotometry and found to reach an endpoint of 4H/1, yielding the neutral PZ radical as determined by EPR. The identity of the stable reduced cluster (2II,2III) was established by electrospray mass spectra of reaction mixtures showing peaks for $[Mn_4O_2L_6]$ (m/z 1555) and $[Mn_4O_2L_5]$ (m/z 1338) after loss of one ligand. The reaction is therefore the first example of a $Mn_4O_4$- cubane-to-$Mn_4O_2$- butterfly core conversion (Scheme 1). The reverse reaction involves the binding of 2 water molecules and removal of 4 H atoms, a reaction that is formally analogous to substrate activation by the WOC. The free energy change for the cubane→butterfly+water reaction in Scheme 1 was estimated to be in excess of the value needed for $O_2$ evolution from water, based on the gas phase bond enthalpy for H atom abstraction from PZH.

Thus, complex 1 is thermodynamically competent to produce $O_2$, but is kinetically prevented from releasing $O_2$. Likewise, the oxidized cubane $1^+$ is capable of reduction by 5 $e^-/4H^+$ to form the $Mn_4O_2L_6$ butterfly, corresponding to an oxidation state change that is formally equivalent to the $S_4$ to $S_{-1}$ states of the WOC.

Milder deoxygenating agents such as $Me_3SiX$ ($X=Cl, N_3$) lead to removal of two oxo bridges from 1 when used in large excess (FIG. 8). For $X=N_3$ the species $[Mn_4O_4X_2L_6]$ ($H^+$) (ESI-MS; m/z 1639) is the dominant species detected in the reaction mixture. This species could either have a cuboidal or butterfly structure in which two $N_3$ ligands replacing 2 oxos. For $X=Cl$, a reactive intermediate forms that releases molecular chlorine ($Cl_2$) at 30–40% yield (vs. 1), while the cluster decomposes and Mn(II) is released.

Unusually Weak Mn-Oxo Bonds in $L6Mn_1O_1$-Cubane.

The kinetics of oxygen atom abstraction from four Mn-oxo complexes were measured in order to calibrate the relative reactivities of different Mn-oxo bond types, including the terminal oxo ($Mn^{III}=O$) in permanganate, the doubly bridging ($\mu_2$-oxo) cores $[Mn^{III}(\mu_2-O)(\mu$-acetate$)_2Mn^{IV}]^{2+}$ and $[Mn^{III}(\mu_2-O)_2(\mu$-acetate$)M^{IV}]^{3+}$, and the triply bridging ($\mu_3$-oxo) cubane core 1. (A. E. M. Boelrijk, G. Ananyev, D. Petrillo, M. Shlyakhova and G. C. Dismukes, unpublished) The bimolecular rate constants for oxo transfer to the phosphine, 1,3,5-triaza-7 phosphatricyclo[3.3. 1.1]decane (PTA) to yield PTAO were measured spectrophotometrically and found to decrease in the following order: $KMnO_4>1>>$ $[Mn_2(\mu-O)(OAc)_2(L^1)_2](BPh_4)_2>[Mn_2(\mu-O)_2(OAc)(L^2)_2]$ $(ClO_4)_3$, with rate constants: $4>0.55>>5.0\times10^{-3}>0.2\times10^{-3}$ ($M^{-1}s^{-1}$), respectively ($L^1=1,4,7$- cyclononane, $L^2=1,4,7$- triazacyclonane, $L^3$=diphenylphosphinic acid). The relative rates indicate an unusually high lability of the $\mu_3$-oxo in cubane 1 compared to the $\mu_2$- oxo cores in both the Mn(2III, IV) dinuclear cores. This faster oxo transfer reactivity is consistent with the longer, weaker ($\mu_3$-O)-Mn bond lengths ($\Delta R>0.1–0.15$ Å) and strained pyramidal geometry vs the shorter, stronger ($\mu_2$-O)-Mn bonds in the planar $Mn_2O$ and $Mn_2O_2$ cores. Moral: Non-planar ($\mu_3$-O)-Mn bonds are unusually weak Mn-oxo bonds.

Protonation and Dehydration Reactions of the $Mn_4O_4L_6$Cubane and Synthesis and Crystal of the Oxidized Cubane $[Mn_4O_4L_6]^+$ The synthesis and crystal structure $[Mn_4O_4L_6]^+(CF_3S)_3^-$), $1^+OTf^-$(L=diphenylphosphinate) is described herein. This molecule extends the known $[Mn_4O_4]^{n+}$ cubane core type to include the $Mn_4$(III,3IV) oxidation state, creating the highest oxidation state Mn-oxo-cubane model complex for the photosynthetic water oxidizing complex (WOC). Deoxygenation of the parent cubane, $Mn_4O_4L_6$, 1, is observed with strong acids and with $Me_3Si(CF_3SO_3)$, by removal of 1 or 2 oxos as $H_2O$ and $(Me_3Si)_2O$, respectively, to form deoxygenated $[Mn_4O_3L_6]^+$ "trigonal" core intermediates with no evidence for dissociation of phosphinate ligands, as seen by mass spectrometry. EPR spectra reveal that $1^+$Otf is paramagnetic with zero-field splitting indicative of an odd-spin ground state and spin multiplicity S=3/2; features which differ from all known EPR signals for the WOC. The isolation of $^+$Otf, the highest oxidation potential Mn-oxo cluster yet synthesized ($E_0$=1.4 V vs. NHE), will enable exploration of new oxidation chemistry, as well as possible pathways for $O_2$ production from water that are related to the mechanism of photosynthetic $O_2$ evolution.

Described herein is the synthesis of an oxidized $Mn_4O_4^{7+}$ core, a potential model for the $S_4$ (or $S_2$) oxidation state of the WOC, determine its crystal structure and demonstrate reduction to the $Mn_4O_4^{6+}$ core.

Complex 1, $Mn_4O_4L_6$, reacts with triflic acid, $CF_3SO_3H$ (HOTf), or trimethysilyl-triflate, $(Me_3Si)CF_3SO_3$ ($Me_3SiOTf$) in the presence of HOTf and oxygen (vide infra) to form $[Mn_4O_4L_6]$ OTf —$CH_3CN$ ($1^+$OTf) which was isolated in ~80% yield from a reaction mixture containing 1+2$Me_3SiOTf$+2 HOTf.

Figure 11:
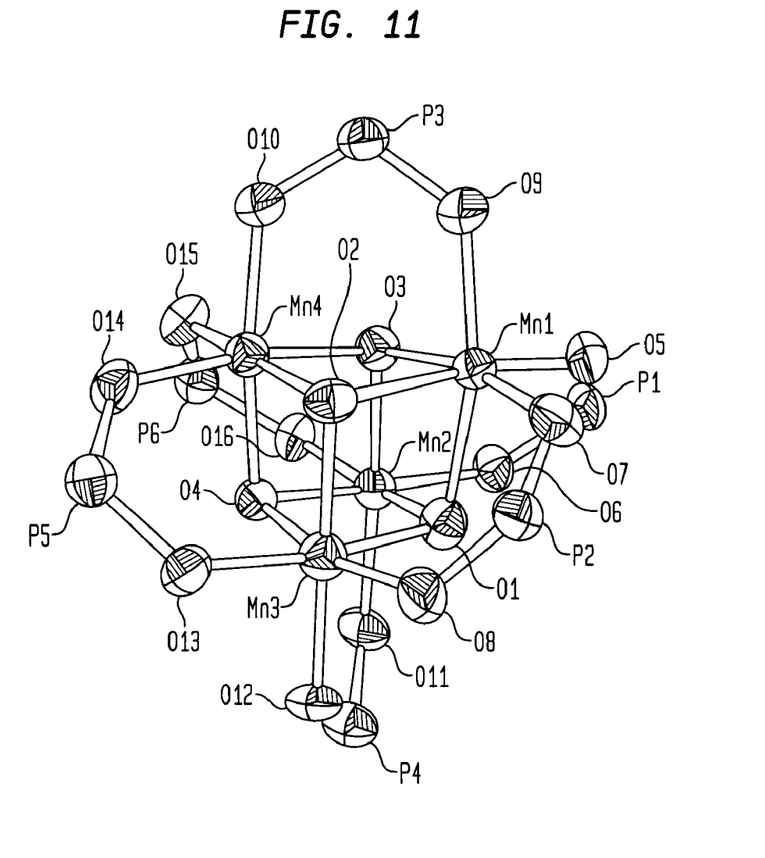

The crystal structure of the inner core of $1^+$OTf.$CH_3CN$ is shown in FIG. 11. Crystals were grown by slow evaporation of a reaction mixture containing 0.3 mM 1 in $CH_2Cl_2$ and 0.6 mM of $Me_3SiOTf$ and HOTf (as 10 mM solutions in $CH_3CN$). A dark brown prism (0.55×0.25×0.20 mm) was mounted on a glass fiber. Data collection was done with a ENRAF NONIUS Kappa CCD system equipped with a molybdenum-target X-ray tube. A total of 84775 reflections were measured (2.2<Θ<30.03), of which 22301 were independent ($R_{int}$=0.0380). Refinement of the structure in the $P_{-1}$ space group was done by full-matrix least-squares fitting on $F^2$ for all reflections except for 8 with very negative $F^2$ and converged at $R_1$=4.03%. Crystal data for 1+OTf, triclinic $P_{-1}$; a=13.8831(1) b=16.7261(2) c=18.7014(2)Å α=110.2338(4) β=97.9111(6) γ=102.5313(6)(deg); Z=2; V=3868.88(7) Å$^3$; d(calc)=1.525 g cm$^{-3}$; T=298 K. Tables of atomic coordinates and anisotropic displacement factors and ortep drawings of the unit cell were obtained.

The cubane cluster shows a significant trigonal distortion from tetrahedral symmetry compared to 1, creating a trigonal pyramidal $Mn_4$ core with shorter $Mn_{2-4}$-O and longer $Mn_1$(apical)-$Mn_{2-4}$(base) bond lengths vs. 1. The mean of the three $Mn_1$(apical)-$Mn_{2-4}$(base) distances in $1^+$OTf is 2.933 Å vs 2.844 Å for the three $Mn_{2-3}$(base)–$Mn_{3-4}$(base) vectors. The short Mn—Mn distances are 0.08–0.14 Å shorter than found in 1, and 0.2–0.1Å longer than in typical dinuclear $[Mn_2O_2]^{3+/4+}$ cores. (Manchandra, R.; Brudvig, G. W.; Crabtree, R. H., Coord. Chem. Rev. 1995, 144, 1–38.) The Mn-O distances reveal elongation around $Mn_1$(avg. 2.004 Å) vs. $Mn_{2-4}$-O(ox)(avg. 1.8948 Å) and 1.952 Å for the Mn-O(oxo) in 1. Also, the narrower O-Mn-O angles around $Mn_1$ (77.58–79.35°) vs. $Mn_{24}$ (82.13–84.8°) indicate a trigonally extended $C_3V$ distortion. The coordinates are consistent with assignment of $Mn_1$ as Mn(III) and $Mn_{2,3,4}$ as Mn(IV). No obvious tetragonal elongation or compression of the Mn-O bonds is observed for Mn(III) in the crystal, in contrast to the carboxylato-bridged trigonally-distorted cubanes with the $[Mn_4O_3X]^{6+}$core ($\mu_3$–X =F$^-$, Cl$^-$Br$^-$, OH$^-$), see Wang, S.; Tsai, H. -L., Hagen, K. S., Hendrickson, D. N., Christou, G., J. Am. Chem. Soc. 1994, 116, 8376–8377; Wang, S., Folting, K., Streib, W. E., Schmitt, E. A., McCusker, J. K., Hendrickson, D. N., Christou, G., Angew, Chem. Int. Ed. Engl. 1991, 30, 305–306; Wang, S., Tsai, H. -L., Streib, W. E., Christou, G., Hendrickson, D. N., J. Chem. Soc., Chem. Commun. 1992, 1427–1430; Aromi, G., Wemple, M. W., Aubin, S. J., Folting, K., Hendrickson, D. N., Christou, G., J. Am. Chem. Soc. 1998, 120, 5850–5851, where axial Jahn-Teller elongations are observed for the three Mn(III) ions.

The results and earlier work (Ruettinger, W., Campana, C., Dismukes, G. C, J. Am. Chem. Soc. 1997, 119, 6670–6671, suggest stronger Mn-phosphinator bonding in $1^+$ and 1 than Mn-carboxylato affinities.

Figure 12:
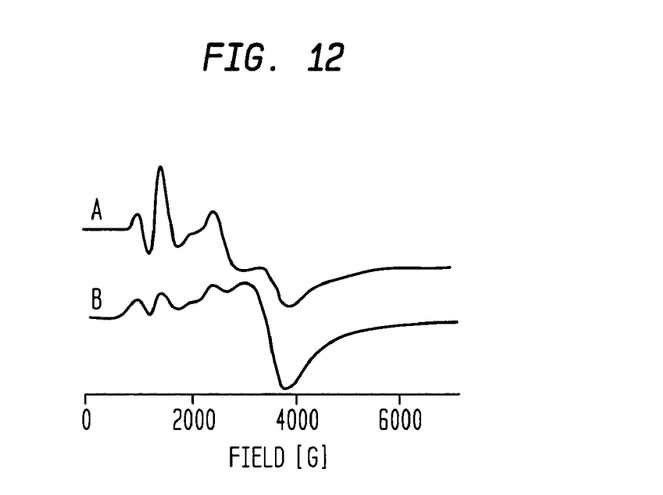
FIG. 12 depicts the EPR spectrum at 6 K of oxidized cubane $1^+$(OTf) in $CH_3Cn$.

Unlike 1, $1^+$OTf is paramagnetic at low temperatures and solutions exhibit intense EPR spectra, as shown in FIG. 12. The signal intensity obeys the Curie Law between 7 and 29K with zero-field splitting and no resolved $^{55}$Mn hyperfine structure. This type of behavior indicates an odd-spin ground states (S=3/2), possibly a high-spin ground state analogous to trigonal $[Mn_4O_6Cl]^{6+}$ complexes in the III$_3$IV oxidation state. [Aubin, 1998 #483] Room temperature electrochemical oxidation of 1 at a platinum electrode ($E_{1/2}$=1.4 V vs. NHE) (Ruettinger, W., Campana, C., Dismukes, G. C., J. Am. Chem. Soc. 1997, 119, 6670–6671) also produces $1^+$, as seen by its EPR signal in FIG. 12, an additional species forms under electrolysis which exhibits a 400 G broad signal at g=2, presumed to arise from a Mn(II) decomposition product. These data establish that formation of $1^+$OTf by acidification of 1 in air involves one-electron oxidation rather than only protonation of 1.

The reaction of 1 with triflic acid in non-aqueous solution leads to an end-point after addition of ~2.5 equivalents of acid that is reversible with a single isosbestic point at 304 nm. $^1$H-NMR reveals formation of a single new species in this reaction with a shifted and paramagnetically broadened pair of peaks at 8.15 and 6.64 ppm with ≧84% yield, identical to a spectrum of crystalline material obtained as described above. The near quantitative yield of $1^+$in solution indicates that it could not form entirely by disproportionation of 1. A requirement for oxygen in the formation of $1_+$OTf from 1+HOTF was established and was examined by NMR and UV-Vis titrations. In deoxygenated solutions the reaction leads to a decreased absorbance change in the 350–450 nm region and also by a shift of the isosbestic point to 307 nm. The oxidation can be reversed by addition of reductants like triethylamine or many common solvents such as MeOH, EtOH, DMF, and DMSO. Addition of 1 eq. $N(CH_3)_3$ leads to quantitative recovery of 1.

The formation of $1^+$ by oxidation of 1 can also be initiated by addition of 2 equivalents of $Me_3SiOTf$, but proceeds to only 50% conversion of 1 and yields 1 eq. $(Me_3Si)_2O$ as measured by NMR. Subsequent addition of 2 equivalents of HOTf leads to complete conversion to $1^+$. ESI-MS (positive ions) spectra of reaction mixtures show the initial formation of the species $[Mn_4O_3L_6]^+$(m/z 1570) independent of whether the reagent is HOTf or $Me_3SiOTf$.

Figure 13:
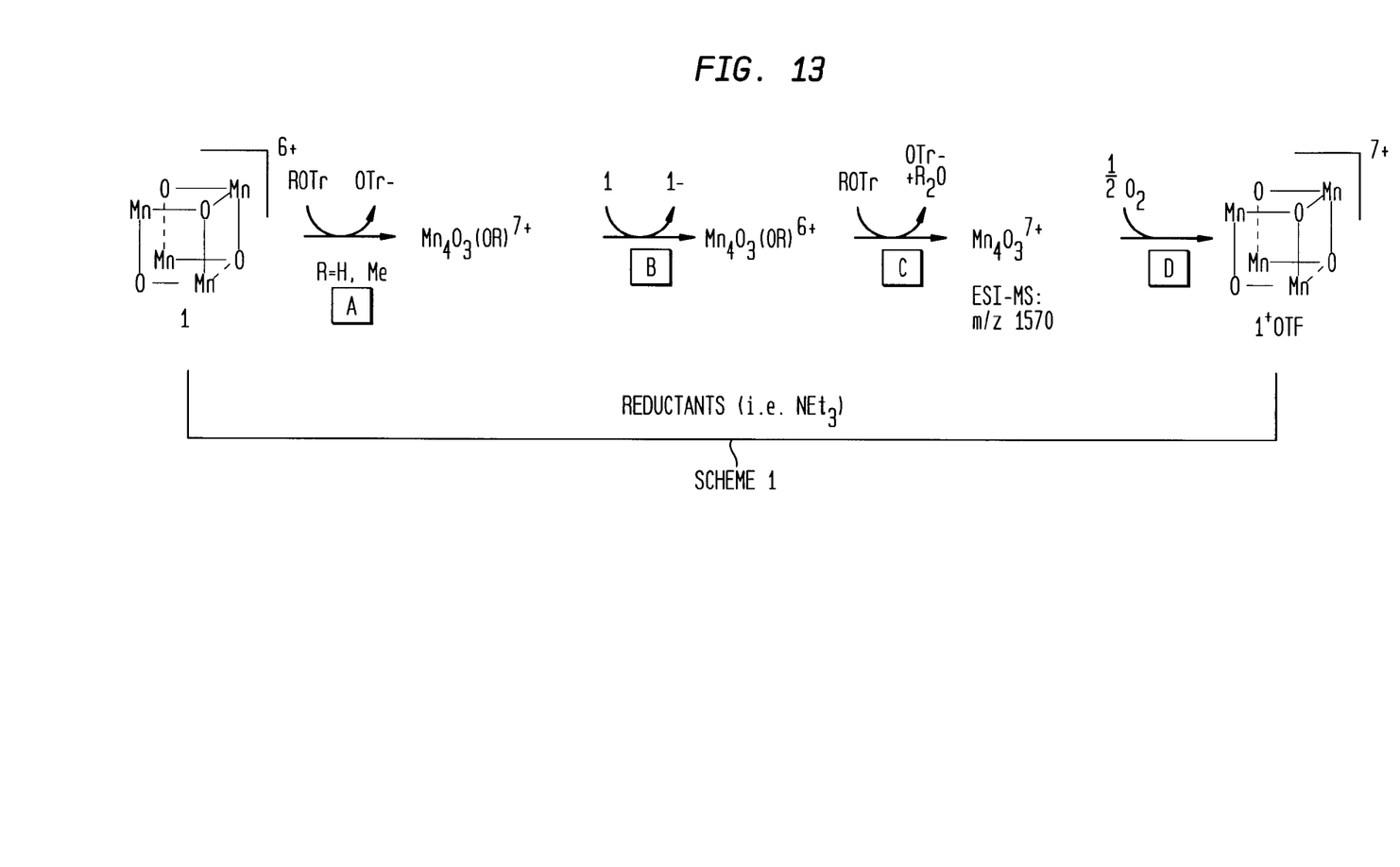
FIG. 13 shows the formation of the oxidized cubane from the parent cubane.

The observed formation of 1+ from 1 is summarized in Scheme 1 of FIG. 13. Initially a proton (from HOTf) or a trimethylsilyl cation (from $Me_3SiOTf$) binds to 1, (Scheme 1, C), yielding $Mn_4O_3(OR)^{7+}$and thus converting it to a stronger oxidant. We propose that this species causes the oxidation of unreacted 1 to $1^+$(D) which limits the yield to only 50% in the case of $Me_3SiOTf$. The resulting one-electron reduced species, $Mn_4O_3(OR)L_6$, continues to react with HOTf or $Me_3SiOTf$ to react with HOTf or $Me_3SiOTf$ to remove one oxide-bridge completely as $OR_2$ (R=H, Me$_3$Si)(E), forming the deoxygented intermediate [Mn$_4$O$_3$L$_6$]$^+$ that is detected by ESI-MS (m/z 1570) and which, in turn, is oxidized by O$_2$ in the presence of protons to form 1$^+$ and water (F). The requirement for HOTf for complete conversion to 1$^+$ in the reaction with Me$_3$SiOTf appears to reflect the necessity to drive the oxidation reaction by thermodynamically favoring release of HOSiMe$_3$.

The isolation of 1$^+$OTf extends the known Mn$_4$O$_4$ cubane core type to include the Mn$_4$(III, 3IV) oxidation state, a possible model for the S$_2$ (Yachandra, V. K.; Sauer, K.; Klein, M. P., Chem. Rev. 1996, 96 2927–2950) or S$_4$ (Zheng, M.; Dismukes, G. C., Inorg. Chem. 1996, 35, 3307–3319) oxidation states of the WOC. The assignment of Mn oxidation states to the S states of the WOC is an unresolved issue, with Mn XANES data [Yachandra, 1996 #444] favoring Mn oxidation states that are two-electrons (sum) more oxidized than those proposed on the basis of $^{55}$Mn EPR data. [Zheng, 1996 #431] The present EPR data for [Mn$_4$O4]$^{7+}$ establish that a trigonally distorted cuboidal core in the III,IV$_3$ oxidation state is indeed incompatible with the EPR properties of the S$_2$ state of the WOC. The S$_2$ state possesses a doublet spin ground state while 1$^+$OTf possesses a higher spin multiplicity ground state. Thus, the S$_2$ state must possess a different core geometry or a different oxidation state (or both). Recent EPR data of the one-electron reduced species, 1$^-$, produced by gamma irradiation have revealed that 1$^-$ possesses a doublet spin ground state and multiline EPR signal belonging to the same class of Mn$_4$ multiline EPR signals as the S$_2$ state multiline signal. [Dismukes, 1998 #484] (Dismukes, G. C.; Ruettinger, W.; Boelrijk, A. e. m., Ho, D., STRUCTURE OF THE Mn$_4$Cal CORE OF THE PSII WATER OXIDIZING COMPLEX AND THE Mn$_4$O$_{-4}$ CUBANE/Mn$_4$O$_2$-BUTTERFLY MODEL COMPLEXES, in Proceedings XIth International Photosynthesis Congress, G. Garob, Editor. 1998, Kluwer Academic: Dordrecht.) Thus, the reduced [Mn$_4$O$_4$]$^{5+}$ cuboidal core is capable of forming a low-spin doublet ground state with a multiline EPR signal reflecting the presence of unpaired spin density on all four Mn ions. On this basis, taken together the present EPR for the oxidized core, l+OTf, support the EPR-derived assignment for the Mn oxidation states of the S$_2$ state as Mn$_4$(111$_3$IV).

The isolation of 1$^+$OTf, the highest oxidation potential Mn-oxo cluster yet synthesized, will enable exploration of new oxidation chemistry with organic and inorganic precursors, as well as possible pathways for O$_2$ production from water that are related to the mechanism of photosynthetic O$_2$ evolution.

The Mn$_4$O$_4$L$_6$ cubane/Mn$_4$O$_2$L6 butterfly family of complexes based on the diphenylphosphinate ligand now spans the oxidation states Mn$_4$(2II, 2III) to (III, 2IV), corresponding to the S$_{-1}$ to S$_4$ oxidation states of the WOC. Our data indicate that a structural transformation (cubane-butterfly) is desirable to stabilize the Mn$_4$ cluster in all six oxidation states. In particular, the Mn$_4$O$_4$L$_6$ cubane core is stable in the Mn$_4$(2II, 2IV) and (III, 3IV) oxidation states, whereas the Mn$_4$O$_2$L$_6$ butterfly core is preferred in the lowest observed oxidation state Mn$_4$(2II, 2III). A distorted cuboidal core Mn$_4$O$_2$X$_2$L$_6$, most likely in the Mn$_4$(4III) oxidation state forms in the reaction with Me$_3$SiN$_3$. A structural rearrangement occurs in the (3III, IV) oxidation state, upon one-electron reduction of 1 which triggers core decomposition (Ruettinger, W.; Campana, C.; Dismukes, G. C., J. Am. Chem. Soc. 1997, 119, 6670–6671), which is now understood to require protons for release of water molecules and stabilization of the butterfly core. This core rearrangement is analogous to a previously conjectured pathway for water binding and oxidation by the WOC. (Vincent, J. B.; Christou, G., Inorg. Chim. Acta 1987, 136, L41–L43) Furthermore, it is consistent with spectroscopic data indicating a structural change with large activation barrier for the S2→S$_3$ step of the WOC. ( Material Karge, M.; Irrgang, K. -D.; Renger, G., Biochemistry 1997, 36, 8904–8913)

Some abbreviations used herein are: PSII (Photosystem II), WOC (Water Oxidizing Complex), EXAFS (Extended X-ray Absorption Fine Structure), ESI-MS (Elelctrospray Ionization Mass Spectrometry), MALDI-TOF (Matric Assisted Laster Desorption Ionization-Time of Flight), HOTf (triflic acid), Me$_3$SiOTf (trimethylsilytriflate), TBAP (tetra-n-butyl ammonium perchlorate), GC-MS (Gas Chromatography-Mass Spectrometry), PZH (Phenothiazine).

Having thus described the invention in detail, it is to be understood that the foregoing description is not intended to limit the spirit and scope thereof. What is desired to be protected by Letters Patent is set forth in the appended claims.

What is claimed is:

1. A manganese-oxo-pyramid complex having the formula L$_6$Mn$_4$O$_3$, wherein Mn$_4$O$_3$, is a pyramidal core and L$_6$ are six bidentate ligands bridging between the Mn atoms.

2. The complex of claim 1, wherein the ligands are carboxylate, phosphinate or diphenylphosphinate ligands.

3. A manganese-oxo-butterfly complex having the formula L$_6$Mn$_4$O$_2$ or L$_5$mn$_4$O$_2$, wherein Mn$_4$O$_2$, is a butterfly core and L$_6$ or L$_5$ are six or five bidentate ligands bridging between the Mn atoms.

4. The complex of claim 3, wherein the ligands are carboxylate, phosphinate or diphenylphosphinate ligands.

5. An improved process for oxidizing a chloride to chlorine in the presence of a catalyst, the improvement comprising reacting the chloride in the presence of a catalyst selected from the group consisting of:

a) a tetramanganese-oxo cubane complex having the formula L$_6$Mn$_4$O$_4$, wherein Mn$_4$O$_4$, is a cubane core and L$_6$ are six facially-capping bidentate ligands bridging between the Mn atoms; and b) a manganese-oxo-pyramid complex having the formula L$_6$Mn$_4$O$_3$, wherein Mn$_4$O$_3$, is a pyramidal core and L$_6$ are six bidentate ligands bridging between the Mn atoms. Mn atoms.

6. The process of claim 5, wherein the ligands are carboxylate, phosphinate or diphenylphosphinate ligands.

7. An improved process for oxidizing water to hydrogen peroxide and oxygen in the presence of a catalyst, the improvement comprising reacting the water in the presence of a catalytic amount of a catalyst selected from the group consisting of:

a) a tetramanganese-oxo cubane complex having the formula L$_6$Mn$_4$O$_4$ wherein Mn$_4$O$_4$, is a cubane core and L$_6$ are six facially-capping bidentate ligands bridging between the Mn atoms; and b) a manganese-oxo-pyramid complex having the formula L$_6$Mn$_4$O$_3$, wherein Mn$_4$O$_3$, is a pyramidal core and L$_6$ are six bidentate ligands bridging between the Mn atoms. Mn atoms.

8. The process of claim 7, wherein the ligands are carboxylate, phosphinate or diphenylphosphinate ligands.

9. A cubical shaped molecule substantially as shown and described in FIG. 2, herein.

10. A cubical shaped molecule substantially as shown and described in FIG. 11, herein.

* * * * *